Nov. 12, 1968 D. L. ARMSTRONG Plant Pat. 2,845
ROSE PLANT
Filed June 9, 1967
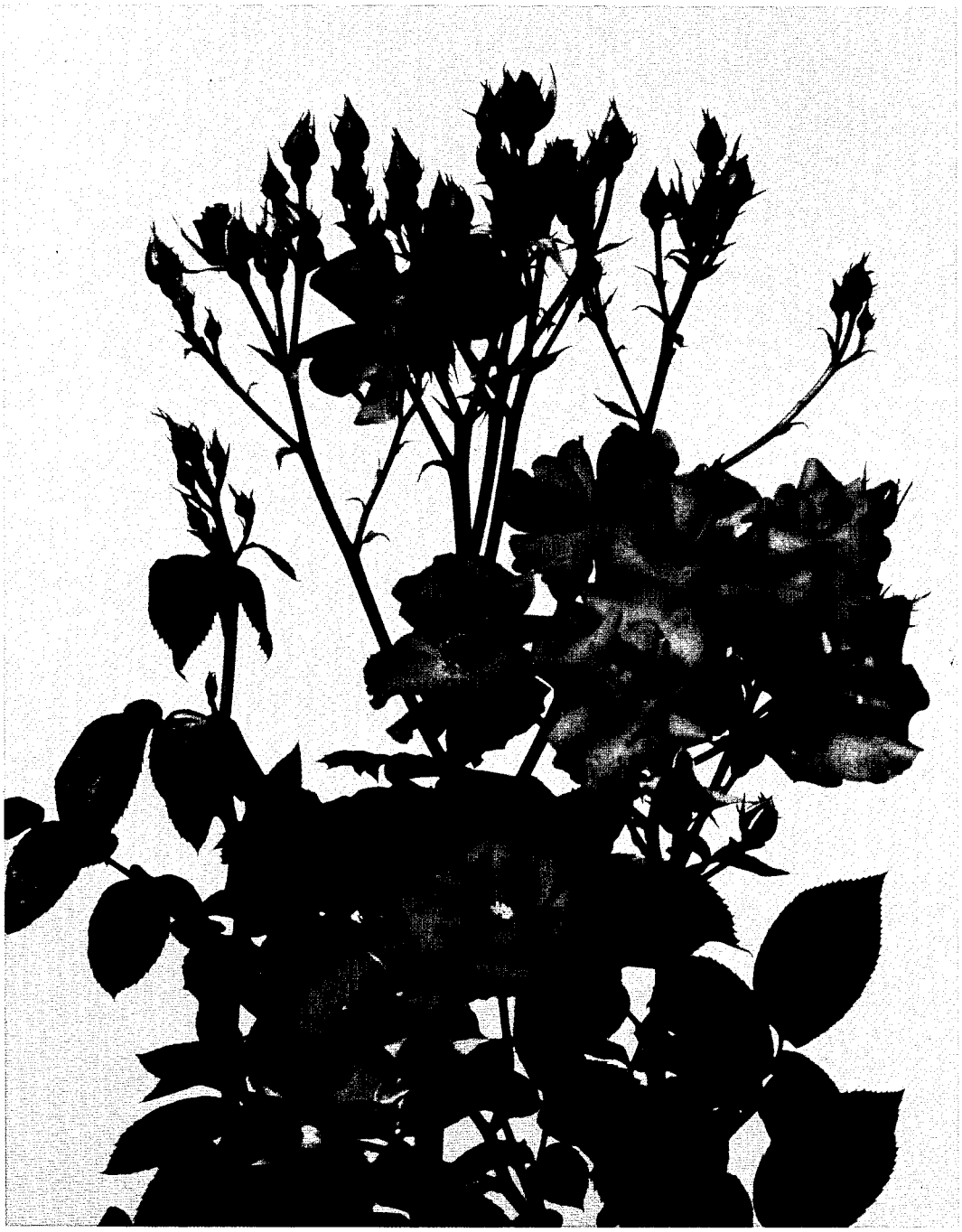
Inventor.
D. L. Armstrong
By: Robb & Robb
Attorneys.

United States Patent Office

Plant Pat. 2,845
Patented Nov. 12, 1968

2,845
ROSE PLANT

David L. Armstrong, Ontario, Calif., assignor to Armstrong Nurseries, Inc., Ontario, Calif., a corporation of California Filed June 9, 1967, Ser. No. 645,067
1 Claim. (Cl. Pit.—29)

The present invention relates to a new and distinct variety of rose plant of the floribunda class, which was originated by me by crossing the rose variety known as "Circus" (Plant Patent No. 1,382) with the variety known as "Ruby Lips" (Plant Patent No. 1,775), the former being the seed parent, and the latter being the pollen parent.

The new variety resulted from an extensive breeding program having for its objective to produce improved floribunda rose varieties in which there are combined the best qualities of each of the parent varieties, but which bear flowers of various colors. This objective was fully achieved in the new variety, as evidenced by the following unique combination of characteristics which are outstanding in the new variety and which distinguish it from its parents, as well as from all other varieties of which I am aware:

(1) A vigorous plant having an attractive, bushy, semi-upright, well-foliaged plant habit;

(2) A very floriferous habit, with the flowers literally covering the plant at peak times and borne in medium sized clusters well spaced over the plant;

(3) Small, moderately double flowers having an attractive open form exposing the center; and (4) A distinctive, attractive and brilliant dark red flower color which is relatively unfading under most weather conditions and presenting a very attractive mass bloom display on the plant.

In comparison with its seed parent, "Circus," the new variety has larger flower clusters, but slightly smaller flowers; the flowers have fewer petals; and the flower color is red as distinguished from the multi-colored flowers of this parent.

As compared with its pollen parent, "Ruby Lips," the new variety has a more upright plant habit than the semi-spreading habit of this parent; the plant is more bushy and more densely foliaged; and the flowers are slightly smaller than the average flower size of this parent.

Asexual reproduction of my new variety by budding, as performed at Ontario, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W)) and Robert Ridgway's Color Standards and Nomenclature (hereinafter abbreviated (R)), as indicated:

Type: Bush; outdoor; seedling; for cut flowers and for garden decoration.
Class: Floribunda.
Breeding: Seedling.
*Seed parent.*—"Circus."
*Pollen parent.*—"Ruby Lips."
Propagation: Holds its distinguishing characteristics through succeeding propagations by budding.

*Flower*

Locality where grown and observed: Ontario, Calif.
Flowers borne: Sometimes singly, but usually from five to ten or more to stem; on strong, short stems.
Quantity of bloom: Very abundant, outdoors.
Continuity: Nearly continuous during growing season.
Fragrance: From slight to moderate.
Bud:
*Peduncle.*—Short; from slender to average caliper; erect; usually smooth; with several to many small stipitate glands and none to few small prickles. Color—near Absinthe Green, Plate XXXI (R), overlaid with near Mineral Red, Plate XXVII (R) on side exposed to sun.
*Before calyx breaks.*—Size—small. Form—short; between ovoid and globular.
*As calyx breaks.*—Color—from Pansy Purple, Plate 928/3, page 177 (W) to Purple Madder, Plate 1028, page 181 (W).
*Sepals.*—Inner surface—with fine, wooly tomentum. Outer surface—usually smooth. Alternate margins—lined with fine, wooly tomentum. Other margins—with few to several small stipitate glands and small, slender foliaceous parts.
*As first petal opens.*—Size—small. Form—short; ovoid. Color: outside—near Purple Madder, Plate 1028/2, page 181 (W); inside—between Indian Lake, Plate 826, page 170 (W) and Ruby Red, Plate 827, page 171 (W), with small area at base of petal near Lemon Yellow; Plate 4, page 4 (W).
*Opening.*—Opens up well; is not retarded or prevented from opening by cold, hot, wet or dry weather.
Bloom:
*Size (when fully open).*—Small; from 2½ inches to 2¾ inches.
*Petalage.*—Double; from 18 to 25 petals plus 0 to 5 petaloids; arranged irregularly.
*Form.*—High-centered at first, but becoming flat to high-centered; petals being at first somewhat loosely cupped, with tips reflexed outward, but later becoming more loosely flat at maturity, with tips reflexed outward.
Petals:
*Texture.*—Medium thickness; leathery.
*Appearance.*—Inside—velvety. Outside—satiny.
*Shape.*—Outside—broadly obovate, with apex flat and sometimes with 1 or 2 notches. Intermediate—broadly obovate, with apex rounded to flat and sometimes with 1 or 2 notches. Inside—obovate, but somewhat irregular, with apex rounded and sometimes with 1 or 2 notches.

This description of a newly opened flower was made from a rose grown outdoors during the months of August-September at Ontario, Calif.

*Color.*—Outer petal: outside surface—near Cardinal Red, Plate 822/1, page 168 (W), blending with near Currant Red, Plate 821/3, page 167 (W) toward base of petal; inside surface—between Cardinal Red, Plate 822/1, page 168 (W) and Chrysanthemum Crimson, Plate 824/2, page 169 (W). Intermediate petal: outside surface—near Cardinal Red, Plate 822/3, page 168 (W), blending with near Rose Madder, Plate 23, page 23 (W) toward base of petal; inside surface—near Cardinal Red, Plate 822/1, page 168 (W). Inner petal: outside surface—same as intermediate petal; inside surface—same as intermediate petal.

This description was made from a rose that was open for three days outdoors during the months of August–September at Ontario, Calif.:

*Color.*—Outer petal: outside surface—between Rose Red, Plate 724/1, page 158 (W) and Tyrian Purple, Plate 727/1, page 159 (W); inside surface—between Cardinal Red, Plate 822, page 168 (W) and Chrysanthemum Crimson, Plate 824/1, page 169 (W). Inner petal: outside surface—same as outer petal; inside surface—same as outer petal.

*General color effect.*—Newly opened flower—between Currant Red, Plate 821/2, page 167 (W) and Cardinal Red, Plate 822/2, page 168 (W). Three days open—between Cardinal Red, Plate 822, page 168 (W) and Chrysanthemum Crimson, Plate 824/1, page 169 (W).

*Behavior.*—Drop off cleanly, not particularly affected by cold, hot, wet or dry weather.

*Flower longevity.*—On bush in garden—4 or 5 days in November. Cut roses grown outdoors and kept at living-room temperatures—2 or 3 days in November.

*Reproductive organs*

Stamens: Average number; arranged regularly about pistils.

Filaments: From short to medium length (from 4 mm. to 8 mm. long); most with anthers.

Anthers: Small; all open approximately at once. Color: upper side—margins near Cadmium Orange, Plate 8/1, page 8 (W), with remainder near Lemon Yellow, Plate 4/2, page 4 (W); under side—margins near Cadmium Orange, Plate 8/1, page 8 (W), with remainder near Lemon Yellow, Plate 4/2, page 4 (W).

Pollen: Moderate quantity. Color—near Tangerine Orange, Plate 9/1, page 9 (W).

Pistils: From few to average number (approximately 40).

Styles: Moderately even; short (from 4 mm. to 6 mm. long); thin; bunched. Color—upper ⅔ of style near Rose Madder, Plate 23/1, page 23 (W), with remainder near Dresden Yellow, Plate 64/3, page 64 (W).

Stigma: Color—near Empire Yellow, Plate 603/1, page 66 (W).

Ovaries: Usually all enclosed in calyx.

Hips: Short; globular; smooth; walls thick and fleshy. Color (mature)—near Carnelian Red, Plate XIV (R).

Sepals: Falling soon; short; curled. Color: inside—near Grayish-Olive, Plate XLVI (R); outside—near Dark Olive-Buff, Plate XL (R).

Seeds: Few (from 2 to 10); medium size.

*Plant*

Foliage:

*Leaves.*—Compound of usually 3 to 7 leaflets; abundant; medium size; leathery; semi-glossy.

*Leaflets.*—Shape—broadly oval. Apex—acute. Base, round. Margin—simply serrate.

*Color.*—Mature: upper surface—near Forest Green, Plate XVII (R); under surface—near Chromium Green, Plate XXXII (R), Young: upper surface, between Light Bice Green, Plate XVII (R) and Chromium Green, Plate XXXII (R); under surface—near Asphodel Green, Plate XLI (R).

*Rachis (the supporting stem of the compound leaf).*—Average size. Upper side—grooved; with few to several stipitate glands on edges. Under side—smooth; with none to few stipitate glands and none to few small prickles.

*Stipules.*—Medium length; medium width; with short to medium length points turning out at an angle of more than 45°.

*Disease resistance.*—Better than average resistance to mildew, as determined by comparison with other floribunda varieties grown under field and garden conditions at Ontario, Calif.

Growth:

*Habit.*—Bushy; upright-spreading; much-branched.

*Growth.*—Vigorous.

*Canes.*—Medium caliper.

*Main stems.*—Color—near Mignonette Green, Plate XXXI (R). Large prickles—several; medium length; hooked slightly downward; with medium length, narrow base; color—near Pinkish-Cinnamon, Plate XXIX (R). Small prickles—from none to few; color—near Pinkish-Cinnamon, Plate XXIX (R). Hairs—none.

*Branches.*—Color—between Courge Green, Plate XVII (R) and Biscay Green, Plate XVII (R). Large prickles—from several to many; from short to medium length; hooked slightly downward; with medium length, narrow base; color—near Pecan Brown, Plate XXVIII (R), Small prickles, from none to few; color—near Pecan Brown, Plate XXVIII (R). Hairs—none.

*New shoots.*—Color—near Apple Green, Plate XVII (R), overlaid with near Buffy Brown, Plate XL (R) on side exposed to the sun. Large prickles—several; from short to medium length; hooked slightly downward; with short to medium length, narrow base; color—near Mineral Red, Plate XXVII (R). Small prickles—from none to few; coor—near Mineral Red, Plate XXVII (R). Hairs, none.

I claim:

1. A new and distinct variety of rose plant of the floribunda class, substantially as herein shown and described, characterized particularly as to novelty by the unique combination of a vigorous plant having an attractive bushy, semi-upright, well-foliaged plant habit, a very floriferous habit, with the flowers literally covering the plant at peak times and borne in medium sized clusters well spaced over the plant, small, moderately double flowers having an attractive open form exposing the center, and a distinctive, attractive and brilliant dark red flower color which is relatively unfading under most weather conditions and presenting a very attractive mass bloom display on the plant.

No references cited.

ROBERT E. BAGWILL, *Primary Examiner.*